United States Patent [19]

Wilber

[11] Patent Number: 5,418,218
[45] Date of Patent: May 23, 1995

[54] HISTIDYL-PROLINE DIKETOPIPERAZINE (CYCLO HIS-PRO) A CNS-ACTIVE PHARMACOLOGIC AGENT

[75] Inventor: John F. Wilber, Baltimore, Md.

[73] Assignee: The University of Maryland at Baltimore, Baltimore, Md.

[21] Appl. No.: 911,639

[22] Filed: Jul. 10, 1992

[51] Int. Cl.$^6$ .......................... C07K 7/64; C07K 5/06; A61K 38/05

[52] U.S. Cl. ........................................ 514/11; 514/19; 530/330

[58] Field of Search .................. 514/11, 19; 530/330

[56] References Cited

U.S. PATENT DOCUMENTS 4,426,378  1/1984  Holaday .............................. 530/330

OTHER PUBLICATIONS

Morley et al., Chem Abstract 94(21):168464u 1983 "Histidyl-proline diketopiperazine decreases food intake in rats".

Borden et al., Chem Abstract 108(25):216563g 1088 "Re-evaluation of histidyl-proline diketopiperazine effects on food intake in rats".

*Primary Examiner*—Jill Warden
*Assistant Examiner*—Carol Salata
*Attorney, Agent, or Firm*—Sughrue, Mion, Zinn, Macpeak & Seas

[57] ABSTRACT

A stable peptide with a direct effect on the central nervous system that can be administered in a general manner, such as orally, is described.

6 Claims, No Drawings

HISTIDYL-PROLINE DIKETOPIPERAZINE (CYCLO HIS-PRO) A CNS-ACTIVE PHARMACOLOGIC AGENT

Portions of the research disclosed herein were supported in part by a grant from the National Institutes of Health.

BACKGROUND OF THE INVENTION

Three major processes could be involved in the pathogenesis of obesity: (1) excess deposition of lipids in adipocytes, (2) reduction of lipid mobilization from adipocytes and (3) decreased lipid utilization.

Until recently, the only factor known to cause excess deposition of fat was a positive energy balance from excess energy intake. Primary adipocyte hyperplasia or increase in enzymes involved in lipogenesis does not play a role in human obesity. (E. L. Bierman and J. Hirsch, Obesity In: R. H. Williams, ed., Textbook of Endocrinology, 6th Ed., Philadelphia, Pa., W. B. Saunders Co., 907–921, 1981). Furthermore, there is no evidence that reductions in lipid mobilization occur. However, decreased lipid utilization is attributable to both reduced physical activity and defective thermogenesis, involving inactivity in children (S. B. Roberts, J. Savage, W. A. Coward, B. Chen and A. Lucas, Energy Expenditure: An Intake in Infants Born to Lean and Overweight Mothers, N. Engl. J. Med., 318:461–466, 1988) and heredity in adults. (E. Ravussin, S. Lillioja, W. C. Knowler et al., Reduced Rate of Energy Expenditure as a Risk Factor for Body Weight Gain, N. Engl. J. Med., 318:467–472, 1988)

Among Pima Indians, Ravussin et al. supra, showed that inherited differences in expenditure of energy contribute importantly to the development of obesity. A difference in basal energy expenditure of 298 Joules per day (J/d) can lead to a mean weight gain of 15.7 kg over 622 days, representing 34% of the total positive energy balance.

Bouchard and coworkers (C. Bouchard, A. Tremblay, J. P. Despres et al., The Response to Long-Term Overfeeding in Identical Twins, N. Engl. J. Med., 322:1477–1482, 1990) studied the response to long-term overfeeding in 12 pairs of identical twins fed an excess of 4200 J/d (6 days per week) for 84 days. The variance between twin pairs was three times greater than within twin pairs. Thus, genetic factors in twins regulate energy storage and energy expenditure.

Stunkard et al. (A. J. Stunkard, J. R. Harris, N. L. Pedersen and G. E. McClearn, The Body-Mass Index of Twins Who have been Reared Apart, N. Engl. J. Med., 322:1483–1487, 1990; A. J. Stunkard, T. I. A. Sorensen, C. Hanis et al., An Adoption Study of Human Obesity, N. Engl. J. Med., 314:193–198, 1986) examined the body mass of 93 identical twin pairs reared separately and 184 pairs reared together. That investigation established that genetic influences on body mass indices in adults are substantial, whereas the childhood environment has little or no influence.

About 1% to 2% of obesity can be ascribed to lesions in hypothalamic appetite regulatory centers, of which the paraventricular nucleus is the most important. The causes of hypothalamic obesity, as reported by Bray and Gallagher, (G. A. Bray and T. F. Gallagher, Manifestations of Hypothalamic Obesity in Man: A Comprehensive Investigation of Eight Patients and a Review of the Literature, Medicine, 54:301–330, 1975) include trauma, adenomas of the third ventricle, inflammatory processes, craniopharyngioma and aneurysms of the internal carotid. Hypothalamic obesity was characterized by sudden-onset hyperphagia and was not due to alterations in energy expenditure, lipolysis, or endocrinopathies.

To understand potential hypothalamic causes of obesity, regulation of normal appetite must be considered. It has been established that the assimilation of nutrients is regulated by a homeostatic system involving both acute and chronic components. Meal size, frequency, and composition are regulated acutely by peripheral elements, including taste perception; by gastric and gastrointestinal satiety factors; and by the hypothalamus, which integrates hormonal, thermal, metabolic and neurogenic signals. Neural regulation occurs in the lateral perifornical region, where $\beta$-adrenergic stimuli inhibit eating.

The most important appetite-inhibiting neuropeptides until this invention include corticotropin releasing hormone, calcitonin gene-related peptide and neurotensin. Generally such neuropeptides will not find general applicability because of the many untoward side effects resulting from the normal primary activities of the neuropeptides.

In addition to peptides, neurotransmitter substances, the most important of which are dopamine and serotonin, can play an inhibitory role in appetite regulation.

A number of peptides stimulate eating, for example, those of the homologous neuropeptide Y family, including neuropeptide Y, neuropeptide YY, and pancreatic polypeptide.

Over longer time intervals, humoral substances, particularly insulin, may participate in the regulation of total body fat mass in the central nervous system. (D. Porte and S. Woods, Regulation of Food Intake and Body Weight by Insulin, Diabetologia., 20:274–280, 1981). This is important because plasma insulin concentrations are correlated precisely and positively with total body fat and are in equilibrium with spinal fluid insulin. Thus, insulin could serve as a central nervous system humoral monitor of total body fat.

Because weight in a given individual appears to vary minimally above and below narrow limits, Keesey (R. E. Keesey, The Body-Weight Set Point: What Can You Tell Your Patients?, Postgrad. Med., 83:114–118, 1988) put forward the concept of a "physiological set point" that controls energy expenditure. It is not known whether such a set point is relevant to human weight regulation. However, animals fed diets with excessive or deficient energy tend to return to their control weights after such diets are terminated. (I. L. Bernstein, E. C. Lotter, P. J. Kulkosky, D. Porte and S. C. Woods, Effects of Force-Feeding Upon Basal Insulin of Rats, Proc. Soc. Exp. Biol. Med., 150:546–548, 1975).

Treating obesity is exceedingly difficult; permanent reversal of obesity is achieved in fewer than 10% of patients after 10 years.

Attaining a negative energy balance is central to the successful management of obesity. Moreover, energy units are equivalent whether they are derived from macronutrient protein, fat, carbohydrate or ethanol. The most appropriate diet for the obese patient is a balanced diet approximating 3600 to 4200 J/d to achieve gradual weight reduction. Very-low-energy diets (<1600 J/d) or total starvation diets are not generally useful, although the previously associated serious or fatal complications are now rarely encountered.

Since 14,700 J equals 0.45 kg of body weight, a negative energy balance of 2100 J/d can achieve a weight loss of approximately 0.45 kg/wk.

Weight loss achieved by diet involves loss of lean body mass (muscle and bone) as well as fat. Thus, because obese individuals are prone to recurrent weight gain, they tend to develop a progressively disproportionate amount of fat in their body composition. Frequent smaller feedings of isoenergy diets, however, do promote weight loss, because consumption of large, intermittent food masses exacerbates abnormal patterns of excessive eating.

A good mechanism for promoting energy expenditure physiologically is by increasing physical activity. Exercise alone, however, is not an efficient means of weight loss, since small amounts of food intake can reverse gains achieved through exercise. Exercise must always be supplemented by diet and, optimally, behavioral modification. Anorexigenic medications also are helpful occasionally.

Drugs have a limited but definite role in combination with the therapies described above. The most useful include the catecholamine congeners diethylpropion hydrochloride (Tenuate, Marion Merrell Dow Pharmaceutical Co., Cincinnati, Ohio), mazindol (Mazanor, Wyeth-Ayerst Laboratories, Philadelphia, Pa.) and phentermine resin (Ionamin, Pennwalt Corp., Rochester, N.Y.); and the indolamine, fenfluramine hydrochloride (Pondimin, AH Robins Co., Richmond, Va.). A large study by the Food and Drug Administration demonstrated that drug therapy can achieve a weight loss of 0.22 kg/wk greater than that with diet alone. (A. C. Sullivan and K. Comai, Pharmacological Treatment of Obesity, Int. J. Obes., 2:167–189, 1978)

Cyclo (His-Pro) (histidyl-proline diketopiperazine) is a cyclic dipeptide derived by limited proteolysis of thyrotropin-releasing hormone (TRH, pGlu-His-ProNH$_2$) through the action of the brain enzyme pyroglutamyl peptidase (C. Prasad and A. Peterkofsky, Demonstration of Two Separate Enzymatic Activities for the Degradation of Thyrotropin-Releasing Hormone in Hamster Hypothalamic Extracts, J. Biol. Chem, 251:3229–3234, 1976; C. Prasad, T. Matsui and A. Peterkofsky, Antagonism of Ethanol Narcosis by Histidyl-Proline Diketopiperazine, Nature, Lond., 268:142–144, 1977).

Since discovery of cyclo (His-Pro) in 1976, the cyclic dipeptide has been shown to elicit a number of endocrine and central nervous system-related biological activities including: (1) elevation of brain cGMP levels (T. Yanagisawa, C. Prasad, J. Williams and A. Peterkofsky, Antagonism of Ethanol-Induced Decrease in Rat Brain cGMP Concentration by Histidyl-Proline Diketopiperazine, A Thyrotropin-Releasing Hormone Metabolite, Biochem. Biophys. Res. Commun., 86:1146–1153, 1979); (2) attenuation of ethanol-induced sleep (C. Prasad et al. (1977) supra); (3) decrease in food intake (J. E. Morley, A. S. Levine and C. Prasad, Histidyl-Proline Diketopiperazine Decreases Food Intake in Rats, Brain Res., 210:465–478, 1981); (4) hypothermia in rats (C. Prasad, T. Matsui, J. Williams and A. Peterkofsky, Thermoregulation in Rats: Opposing Effects of Thyrotropin-Releasing Hormone and its Metabolite Histidyl-Proline Diketopiperazine, Biochem. Biophys. Res. Commun., 85:1582–1587, 1978); (5) attenuation of ketamine-induced anesthesia (H. Bhargava, Antagonism of Ketamine-Induced Anesthesia and Hypothermia by TRH and Cyclo (His-Pro), Neuropharmacology, 20:699–702, 1981); (6) inhibition of dopamine uptake by rat brain striatal synaptosomes (F. Battaini and A. Peterkofsky, Histidyl-Proline Diketopiperazine; An Endogenous Brain Peptide that Inhibits Na+/K+ ATPase, Biochem. Biophys. Res. Commun., 94:240–247, 1980); and (7) inhibition of prolactin secretion in vitro (K. Bauer, K. J. Graf, A. Faivre-Bauman, S. Beier, A. Tixier-Vidal and H. Kleinhauf, Inhibition of Prolactin Secretion by Histidyl-Proline Diketopiperazine, Nature, 274:174–175, 1978; S. Melmed, H. E. Carlson, R. Rand and J. M. Hershman, Histidyl-Proline Diketopiperazine Suppresses Prolactin Secretion in a Human Pituitary Cell Line, Endocrinology, 106:699A, 1980; C. Prasad, J. F. Wilber, V. Akerstrom and A. Banerji, Cyclo (His-Pro): A Selective Inhibitor of Rat Prolactin Secretion In Vivo, Life Sci., 27:1979–1983, 1980).

A number of the biological activities associated with cyclo (His-Pro) are similar to those of TRH (H. Bhargava et al. (1981) supra; R. L. Gebhard, J. E. Morley, W. F. Prigge, M. W. Goodman and C. Prasad, TRH and Histidyl-Proline Diketopiperazine Inhibit Cholesterol Synthesis in Dog Intestine, Peptides 2:137–140, 1981; J. E. Morley et al. (1981) supra; Co Prasad et al. (1977) supra; and T. Yanagisawa et al. (1979) supra) whereas other activities either are opposite to those of TRH (K. Bauer et al. (1978) supra; S. Melmed et al. (1980) supra; C. Prasad et al. (1978) supra; and C. Prasad et al. (1980) supra) or completely unrelated to those of TRH (F. Battaini and A. Peterkofsky (1980) supra). In addition there are known TRH-related biological functions that are unique to TRH and cyclo (His-Pro) has not been shown to possess the ability to effect those functions (C. Prasad et al. (1977) supra and C. Prasad et al. (1980) supra).

SUMMARY OF THE INVENTION

It is an object of the instant invention to provide a composition and method for the treatment of a variety of biologic functions resulting from mid-brain activity using a compound that need not be administered directly into the brain.

That and other objects have been achieved in the development of a method for influencing biologic functions resulting from mid-brain activity, such as dampening hunger and thereby resulting in weight loss, by the non-central nervous system administration of cyclo (His-Pro).

Histidyl-proline diketopiperazine (cyclo His-Pro) is related to thyrotropin releasing hormone (TRH). Cyclo (His-Pro) can be obtained by enzymatic reaction of TRH with pyroglutamyl peptidase which has the effect of removing the glutamine residue, for example, pGlu-peptidase obtained from Aerobacter cloacae can be used to cleave the terminal pyroglutamic acid residue from TRH.

Alternatively, cyclo (His-Pro) can be synthesized from the requisite amino acid starting materials as known (Prasad et al. (1977) supra).

Cyclo (His-Pro) also is available commercially from Sigma (St. Louis, Md.) however, that product is not suitable for ingestion.

As noted hereinabove, the beneficial effects of cyclo (His-Pro) are obtained when the dipeptide is present at key areas of the brain, for example, the hypothalamus. But earlier studies were relegated to direct administration of cyclo (His-Pro) to the targeted areas of the brain by stereotactic techniques. A key feature of the instant invention is the ability of administering cyclo (His-Pro) by means other than direct administration to the central nervous system, namely the brain.

Cyclo (His-Pro) provides unexpected benefits, possibly arising from the unique structure thereof. The dipeptide is resistant to enzymatic degradation in vivo and thus presents with a long half-life. While it is known that the pyroglutamic acid residue often confers stability on a peptide carrying the same at a terminus, such as TRH, the precursor of cyclo (His-Pro), the pyroglutamic acid residue is not present in cyclo His-Pro.

Furthermore, as an endogenous compound, cyclo (His-Pro) will be non-immunogenic and present a lowered risk of morbidity. As noted hereinabove, cyclo (His-Pro) is found in the peripheral circulation and in many tissues (Hitton et al., Neuropeptides (1990) 15:55–59 and Kandarakis et al., Neuropeptides (1985) 6:21–25). Thus, as a self-molecule, cyclo (His-Pro) is an ideal candidate for in vivo use.

For example, in contrast to other inhibiting peptides, cyclo (His-Pro) can reduce appetite for as long as 12 hours after intracerebroventricular administration to rodents, and weight gain can be inhibited for 2 weeks when cyclo (His-Pro) is infused into the lateral ventricle. In addition, concentrations of cyclo (His-Pro) undergo fluctuations in the hypothalamus in relation to nutrient events that suggest its potential physiological relevance as a satiety regulator (J. F. Wilber, Regulation of Appetite by Peptides and Monamines. In: L. DeGroot, ed., Endocrinology, 2nd ed., Philadelphia, Pa.: W. B. Saunders Co., 2769–2776, 1989). Cyclo (His-Pro) concentrations rise approximately 30% in the hypothalamus during fasting and then return promptly to prefeeding levels within 60 minutes.

Those changes suggest that secretory inhibition of cyclo (His-Pro) during fasting stimulates eating, and the secretion of cyclo (His-Pro) during refeeding can initiate satiety. Moreover, cyclo (His-Pro) concentrations are higher in the paraventricular nucleus than in other hypothalamic nuclei in rodent. (J. F. Wilber, M. Mori, J. Pegues and C. Prasad, Endogenous C(HP): A Potential Satiety Neuropeptide in Normal and Genetically Obese Rodents, Trans. Assoc. Am. Physicians, 98:131–136, 1982)

Thus, it was determined in the development of the instant invention that cyclo (His-Pro), unlike the vast majority of biologics that are susceptible to degradation in the gastrointestinal tract, can be administered by those routes normally employed for drug administration, such as intramuscularly and intravenously, but also that cyclo (His-Pro) can be administered orally. Notably, treatment of most central nervous system disorders, and primarily treatment of the brain, is impeded by the blood-brain barrier. Although not an absolute barrier of the passage of compounds into the brain, many compounds cross very slowly if at all to any effective extent. It has been determined that cyclo (His-Pro) crosses the blood-brain barrier to achieve effective concentrations in a short period of time.

As noted hereinabove, cyclo (His-Pro) elicits a number of activities including attenuation of ethanol-induced narcosis, hypothermia, attenuation of ketamine-induced anesthesia and decreased food intake. Those and other activities of cyclo (His-Pro) are contemplated to fall within the scope of the invention as it is now possible to administer the drug by means other than directly to the brain.

It is likely, in view of the observation of incremental activities in response to cyclo (His-Pro) administration, that cyclo (His-Pro) may be useful when used in concert with other known pharmaceuticals with similar activities. Thus, in the forum of weight control, cyclo (His-Pro) may be used in combination with an amphetamine-like drug, such as diethylpropion, prazindol and phenterimine; flenfluramine or with the drug Prosac.

In the area of weight loss, the use of cyclo (His-Pro) can have incidental benefits. For example, it is known that the onset of Type II diabetes mellitus can be triggered by obesity. Thus, the onset of diabetes mellitus can be delayed or prevented by controlling weight gain using cyclo (His-Pro). In another example, hyperlipoproteinemia associated with obesity also can be precluded by monitoring and preventing weight gain using cyclo His-Pro.

As to the active ingredient, while the effect as to weight loss appears to be stereospecific, it is contemplated that alterations can be made to the compound to enhance the activities thereof contemplated to fall within the scope of the instant invention. Thus, while cyclo (Glu-Phe) and cyclo (Pro-Pro) did not provide weight loss activity, modification of either the histidine, proline or equivalent amino acid can enhance an activity. For example, methylated TRH wherein the histidine is methylated at the 3′ position has a fifteen-fold greater activity than native TRH.

Specific delivery of the active ingredient may be accomplished by any of a variety of known means. Examples of acceptable delivery systems include injections with a needle and syringe, injections with an air gun, surgical implantation of a reservoir and oral preparations such as syrups, tablets, pills and capsules.

While it is possible for the active ingredient to be administered as a raw chemical, it is preferable to present the active ingredient as a pharmaceutical formulation, within the scope of the present invention, comprising non-essential ingredients meant to sustain the activity of the active ingredient as well as enhance certain desirable properties of the final preparation, such as buffers, stabilizers, preservatives, glidants and the like. The carrier(s) must be "acceptable" in the sense of being compatible with other ingredients of the formulation and not deleterious to the recipient thereof. Thus, it is understood that the treatment described herein may include the step of bringing into association the active ingredient with a liquid carrier and then locally delivering the formulation. Formulations suitable for administration conveniently comprise sterile aqueous solutions of the active chemical, which may be conveniently prepared by mixing the active chemical with water, and after rendering said solution sterile it may be presented in sealed containers. Notably, it has been found that the active compound can be added to water, such as drinking water from the tap, and retain effectiveness.

Pharmaceutical formulations can be of solid form including tablets, capsules, pills, bulk or unit dose powders and granules; and also in liquid form including solutions, fluid emulsions, fluid suspensions, semisolids and the like. In addition to the active ingredient, the formulation would comprise suitable art-recognized diluents, carriers, fillers, binders, emulsifiers, surfactants, water-soluble vehicles, buffers, solubilizers and preservatives.

Modes of administration include those known in the art for administering biologically active agents. For example, an active ingredient-containing solution can be delivered intravenously, by a pump means attached to a reservoir containing bulk quantities of said solution, contained in liposomes or other micro delivery vehicles by passive diffusion from an implant, such as a Silastic implant or Alzet pump, and the like. The making of administrable forms is known in the pharmaceutic arts.

The skilled artisan can determine the most efficacious and therapeutic means for effecting treatment practicing the instant invention. Reference can also be made to any of numerous authorities and references including, for example, "Goodman & Gilman's, The Pharmaceutical Basis of Therapeutics" (6th ed., Goodman et al., eds., MacMillan Publ. Co., N.Y., 1980).

A suitable oral dosage in primates, including man, is in the range of 0.01–20 mg/kg/day. As to parenteral routes, the dosage generally can be lowered, for example 0.01–5 mg/kg/day. In any event, it would not require undue experimentation for the artisan to ascertain suitable dosage regimens based on animals studies and clinical studies. In the art of neurochemistry, the rat is the standard animal model. It is not uncommon for rat studies to serve as the basis for the development of a therapeutic agent and method. Typical toxicity, morbidity and mortality studies are practiced using known techniques. In humans, cyclo (His-Pro) preferably is administered in an oral form.

As revealed in the instant invention, cyclo (His-Pro) can be added to the drinking water and still exert the requisite satiety activity. It also is contemplated that cyclo (His-Pro) can be a diet supplement not only as a pill to be taken daily, such as a vitamin tablet, but that the active agent can be added to a variety of foods and ingested as part of the daily diet. Thus, cyclo (His-Pro) can be added to drinks, snacks, specially prepared dieter's meals and the like to serve as a means of weight control. The cyclo (His-Pro) can be added as a liquid to the food or sprinkled on as a powder, the exact form and means of delivery is not critical to the instant invention.

The invention now will be exemplified further by way of the following non-limiting examples.

EXAMPLE 1

About 40 μmol of TRH was incubated in about 50 μmol Tris-HCl (pH 7.5) containing about 800 μl of Aerobacter cloacae pGlu-peptidase (purified up to the Sephadex G-100 stage as described by Doolittle and Armentrout (Biochemistry (1968) 7, 516–521) with an activity of about 0.3 μmol pGlu-Ala hydrolysed $min^{-1}$ $ml^{-1}$) for about 3 hours at about 25° C. in a total volume of about 1 ml. The resulting cyclic peptide was purified from the reaction mixture.

EXAMPLE 2

Synthetic L-histidyl-L-proline diketopiperazine was prepared by coupling benzyloxycarbonyl-L-histidine (about 20 mmol, ICN) with L-prolineamide (about 20 mmol, Vega-Fox) in the presence of hydroxybenzotriazole (about 40 mmol, Aldrich), N-ethylmorpholine (about 20 mmol, Aldrich) and dicyclohexylcarbodiimide (about 20 mmol, Pierce). The solution in about 175 ml of dimethylformamide was stirred in an ice-bath for about 3 hours and then overnight at room temperature.

After removal of the precipitated dicyclohexylurea, the solution was concentrated to dryness in vacuo, then dissolved in approximately 25 ml of $H_2O$. The solution was applied to a column (3×20 cm) of diethylaminoethylcellulose (Whatman DE-23, free base) previously equilibrated with $H_2O$ and eluted with $H_2O$ (10-ml fractions). Those fractions which were Pauly positive (R. M. C. Dawson, D. C. Elliott, W. H. Elliott and K. M. Jones (eds.) "Data for Biochemical Research" p. 229, Clarendon, Oxford, 1959) were pooled and concentrated to dryness in vacuo.

The intermediate compound, benzyloxycarbonyl-L-histidyl-L-prolineamide was crystallized four times from hot $H_2O$ (yield approximately 500 mg; micro-analysis for C,H,N,O, (Microanalysis, Inc., Wilmington, Del.) showed (in %): 58.94, 6.04, 18.04, 16.90). The calculated values are: 59.21, 6.02, 18.17, 16.60. Benzyloxycarbonyl-L-histidyl-L-prolineamide (about 500 mg) was dissolved in a solution containing methanol (about 10 ml), $H_2O$ (about 0.3 ml) and glacial acetic acid (about 0.3 ml). After adding palladium black catalyst (about 100 mg), the suspension was hydrogenated under about 40 pounds pressure for about 2 hours. The catalyst was removed by filtration and the resultant solution was heated in a boiling $H_2O$ bath for about 30 minutes, then dried in vacuo.

After dissolving the product in $H_2O$, it was purified by passage through a column (2×5 cm) of DEAE-cellulose and the column was washed with $H_2O$. The Pauly-positive fractions were concentrated to dryness in vacuo to yield crystalline L-histidyl-L-proline diketopiperazine (yield approximately 200 mg). Microanalysis for C,H,N,O showed (in %): 54.75, 6.08, 22.10, 17.22. The calculated values for His-Pro.0.6 $H_2O$ are: 53.91, 6.25, 22.86, 16.97.

Mass spectrographic analysis showed prominent ions at m/e 234 (the molecular ion of His-Pro), m/e 154 (the proline-glycine diketopiperazine ion), m/e 81 (the methyl imidazole ion) and m/e 70 (the pyrroline ion). $^1H$-magnetic resonance spectral analysis at 100 MHz showed chemical shifts at 1.95, 2.2, 3.4, 3.5, 4.65, 7.4 and 8.25 p.p.m. downfield from trimethylsilane. Amino acid analysis of an acid hydrolysate (6 M HCl, 15 pounds $inch^{-2}$, 180 minutes) showed the presence of ninhydrin-positive material corresponding only to proline and histidine (ratio 1.1:1).

EXAMPLE 3

Cyclo (His-Pro) is uniquely resistant to proteolytic digestion by pancreatic or intestinal enzymes. When the substance is administered orally to rats, it appears in the plasma completely unaltered biochemically. Experimental studies show that cyclo (His-Pro) induction of weight loss is due to induction of satiety, not of nausea, vomiting or illness. Because of its uniquely long duration of action of about 12 hours (administered IVT acutely) and the fact that it can be administered orally without proteolytic degradation, cyclo (His-Pro) has been given orally to rodents in dosage schedules of 1 or 2 mg/kg/day for 14 to 18 days. In a representative experiment, control animals on normal drinking water without cyclo (His-Pro) gained from a mean of 248 to 396 gms, whereas experimental animals receiving cyclo (His-Pro) gained only a mean of 384 gms, representing an inhibition of weight gain of 12 grams (minus 8.1%), statistically significant at P<0.02. Cyclo (His-Pro) also can induce inhibition of appetite in animals when given intraperitoneally, for example in a dosage schedule of 20 mg/kg/day for 24 days in animals receiving liquid diets. The effect observed is seen as an inhibition of weight gain and not so much as a weight loss.

All references cited herein are incorporated by reference in their entirety.

The described embodiments are to be considered illustrative and not restrictive. The scope of the invention is, therefore, indicated by the appended claims rather than the foregoing description. All changes that come within the meaning and range of equivalency are to be embraced within the scope of the invention.

I claim:

1. A method comprising administering to a primate orally an effective amount of histidyl-proline diketopiperazine (cyclo (His-Pro)) for enhancing satiety.

2. The method of claim 1, wherein said cyclo (His-Pro) is added to a food.

3. A method of controlling food intake in a primate comprising administering to said primate orally an amount of cyclo (His-Pro) effective to enhance satiety.

4. The method of claim 3, wherein said cyclo (His-Pro) is added to a food.

5. A method comprising orally administering to a primate an amount of cyclo (His-Pro) effective for enhancing satiety.

6. The method of claim 5 wherein said cyclo (His-Pro) is added to a food.

* * * * *